(12) United States Patent
Lee et al.

(10) Patent No.: US 8,298,155 B2
(45) Date of Patent: Oct. 30, 2012

(54) PURE TONE AUDIOMETER WITH AUTOMATED MASKING

(75) Inventors: Dong Hoon Lee, Gyeongsangnam-do (KR); Jin Dong Kim, Busan (KR); Yun Sung Ro, Seoul (KR); Jung Hwan Ok, Gyeonngi-do (KR); Kyu Won Lee, Busan (KR)

(73) Assignee: UMedical Co., Ltd., Busan (KR)

( * ) Notice: Subject to any disclaimer, the term of this patent is extended or adjusted under 35 U.S.C. 154(b) by 698 days.

(21) Appl. No.: 12/441,353

(22) PCT Filed: Jul. 27, 2007

(86) PCT No.: PCT/KR2007/003638
§ 371 (c)(1),
(2), (4) Date: Mar. 13, 2009

(87) PCT Pub. No.: WO2008/032927
PCT Pub. Date: Mar. 20, 2008

(65) Prior Publication Data
US 2009/0288489 A1    Nov. 26, 2009

(30) Foreign Application Priority Data

Sep. 14, 2006  (KR) .................. 10-2006-0088931

(51) Int. Cl.
*A61B 5/00* (2006.01)
*H04R 29/00* (2006.01)
(52) U.S. Cl. ........................ 600/559; 381/60
(58) Field of Classification Search ................ 381/600, 381/60; 600/559
See application file for complete search history.

(56) References Cited

U.S. PATENT DOCUMENTS

| | | | |
|---|---|---|---|
| 6,964,642 B2 | 11/2005 | Wasden et al. | |
| 7,018,342 B2 | 3/2006 | Harrison et al. | |
| 7,037,274 B2 | 5/2006 | Thornton et al. | |
| 7,695,441 B2 * | 4/2010 | Harrison et al. | 600/559 |
| 7,736,321 B2 * | 6/2010 | Wasden et al. | 600/559 |
| 2004/0071295 A1 * | 4/2004 | Wasden et al. | 381/60 |
| 2004/0071296 A1 * | 4/2004 | Wasden | 381/60 |
| 2004/0073134 A1 * | 4/2004 | Wasden et al. | 600/559 |
| 2004/0073135 A1 * | 4/2004 | Wasden et al. | 600/559 |
| 2004/0073136 A1 * | 4/2004 | Thornton et al. | 600/559 |
| 2010/0217149 A1 * | 8/2010 | Harrison et al. | 600/559 |
| 2010/0268115 A1 * | 10/2010 | Wasden et al. | 600/559 |

FOREIGN PATENT DOCUMENTS

KR     10-345371      2/2001

* cited by examiner

*Primary Examiner* — Max Hindenburg
*Assistant Examiner* — Sean Dougherty
(74) *Attorney, Agent, or Firm* — Charles A. Lemaire; Lemaire Patent Law Firm, P.L.L.C.

(57) ABSTRACT

The present invention relates to a pure tone audiometer, and more particularly, to a pure tone audiometer with automated masking which is capable of automatically performing air-conduction and bone-conduction hearing tests and automatically performing a masking test, if necessary, so that a person obtains an accurate pure tone hearing threshold without others' assistance. The pure tone audiometer of the present invention can accurately perform the pure tone hearing test with automated masking without assistance from a doctor or an audiologist. Thus, with the pure tone audiometer, people can easily check their hearing ability for prevention and early detection of hearing loss and take swift action to cure hearing loss.

20 Claims, 1 Drawing Sheet

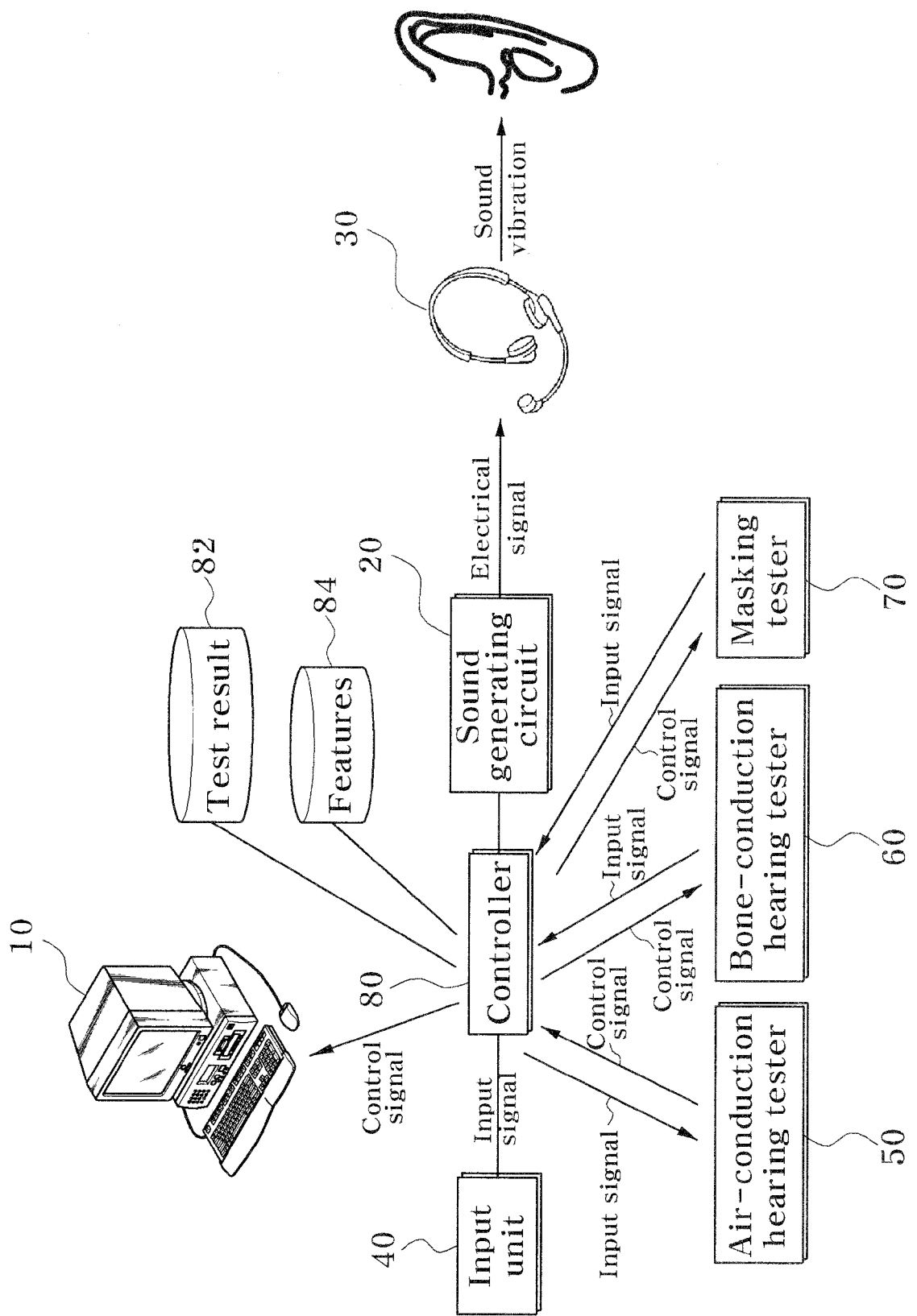

PURE TONE AUDIOMETER WITH AUTOMATED MASKING

CROSS-REFERENCE TO RELATED APPLICATIONS

This U.S. national-stage application under 35 U.S.C. 371 claims the benefit under 35 U.S.C. §119(a)-(d), 35 U.S.C. §365(a)-(c), and 37 CFR §1.55 of International Application Number PCT/KR2007/003638, with an international filing date of Jul. 27, 2007 (International Publication Number WO 2008/032927, with a publication date of Mar. 20, 2008), and of Korean Patent Application Number 10-2006-0088931 filed on Sep. 14, 2006 (to which Application PCT/KR2007/003638 claimed priority), each of which is incorporated herein by reference in its entirety.

FIELD OF THE INVENTION

Technical Field

The present invention relates to a pure tone audiometer, and more particularly, to a pure tone audiometer with automated masking which is capable of automatically performing air-conduction and bone-conduction hearing tests and automatically performing a masking test, if necessary, so that a person obtains an accurate pure tone hearing threshold without others' assistance.

BACKGROUND OF THE INVENTION

Background Art

The senses of hearing and sight are important perception means for obtaining information in modern information society. However, as industrialization has progressed, noise has increased around work places, homes, etc., and noise induced hearing loss has increased.

Most hearing loss, except for some kinds of rapid hearing loss, appears slowly and unconsciously. To cure hearing loss, early detection and proper measures of hearing loss is required. Early detection may require periodic visits to a hospital to undergo hearing tests, but often people cannot afford to go to the hospital.

Korean Patent No. 10-345371 describes a method to solve this problem by performing a hearing test in a web environment. This method includes only a pure tone test without noise-based masking. Accordingly, when a difference in an air-conduction hearing threshold between both ears is 35 dB or more, or when a difference between an air-conduction hearing threshold of an ear with bad hearing (hereinafter referred to as a "bad ear") and a bone-conduction hearing threshold of an ear with good hearing (hereinafter referred to as a "good ear") is 15 dB or more, the method cannot accurately measure hearing loss. As a result, a pure tone hearing test with masking may have to be performed again at a hospital by a well trained audiologist or doctor in order to obtain a more accurate test result. Here, masking prevents erroneous measurements that may occur when, upon measuring a hearing threshold of the bad ear, a person with a great hearing difference between his/her left and right ears first hears sound with the good ear.

Hearing the sound with the other ear upon measuring one ear's hearing is called shadow hearing or cross hearing, however, a masking noise can be applied to the good ear to prevent the shadow hearing. For masking in air-conduction and bone-conduction hearing, there are a method for calculating a masking amount using a formula, and a manual method by which an audiologist or a doctor well trained for a psychoacoustic method can directly calculate a masking amount.

However, since this test method requires an audiologist or a doctor's assistance and takes a long time, taking swift action may be impossible and, since a person may visit a hospital after having suffered from severe hearing loss, early detection of hearing loss may be difficult.

SUMMARY OF THE INVENTION

Disclosure of Invention

Technical Problem

The present invention is directed to a pure tone audiometer with automated masking which is capable of easily performing an accurate pure tone hearing test without a specialist's assistance, enabling prevention and early detection of hearing loss and swift action to cure hearing loss.

Technical Solution

One aspect of the present invention provides a pure tone audiometer comprising: a display unit for displaying a use-procedure guide or a result of a pure tone hearing test; a sound generating circuit for generating and outputting an electrical signal in response to a control signal; an output unit including a headphone and a bone-conduction vibrator, and receiving the electrical signal from the sound generating circuit to generate and output a pure tone or a noise for the pure tone hearing test; an input unit for allowing a user hearing the pure tone generated by the output unit to input a response to the tone; an air-conduction hearing tester for performing the pure tone hearing test based on a pure tone propagated via an external auditory meatus by outputting a control signal to control the headphone of the output unit to generate the pure tone and by adjusting the pure tone depending on a response from the user; a bone-conduction hearing tester for performing the pure tone hearing test based on a pure tone propagated through a skull by outputting a control signal to control the bone-conduction vibrator of the output unit to generate the pure tone and by adjusting the pure tone depending on a response from the user; a masking tester for performing a hearing test by outputting a control signal to generate a masking sound to one ear having good hearing (a good ear) and the pure tone to the other ear when there is a difference of 35 dB or more between both ears' hearing measured by the air-conduction hearing tester, or when there is a difference of 15 dB or more between a air-conduction hearing threshold of the ear having bad hearing (a bad ear) and a bone-conduction hearing threshold of the good ear measured by the bone-conduction hearing tester; and a controller for outputting the control signal to control the sound generating circuit to generate the masking sound in response to a control signal from the air-conduction hearing tester, the bone-conduction hearing tester, and the masking tester, sending the response of the user from the input unit to the air-conduction hearing tester, the bone-conduction hearing tester, and the masking tester, and outputting a control signal to control the display unit to display the use-procedure guide and the test result when the air-conduction hearing tester, the bone-conduction hearing tester, and the masking tester proceed to the hearing test.

Preferably, the controller comprises a storage unit for storing the result of the pure tone hearing test, such that a type and degree of hearing loss are displayed.

Preferably, the controller stores features of various types of sound generating circuits, headphones, and bone-conduction vibrators, and outputs a different electrical signal depending on used ones of the sound generating circuits, headphones, and bone-conduction vibrators.

Advantageous Effects

As described above, the pure tone audiometer of the present invention can accurately perform the pure tone hearing test with automated masking without assistance from a doctor or an audiologist. Thus, with the pure tone audiometer, people can easily check their hearing ability for prevention and early detection of hearing loss and take swift action to cure hearing loss.

BRIEF DESCRIPTION OF THE DRAWINGS

FIG. 1 is a block diagram of a pure tone audiometer according to the present invention.

DESCRIPTION OF THE INVENTION

Mode for the Invention

Hereinafter, exemplary embodiments of the present invention will be described in detail. However, the present invention is not limited to the exemplary embodiments disclosed below, but can be implemented in various types. Therefore, the present exemplary embodiments are provided for complete disclosure of the present invention and to fully inform the scope of the present invention to those ordinarily skilled in the art.

Referring to FIG. 1, a pure tone audiometer of the present invention comprises a display unit 10, a sound generating circuit 20, an output unit 30, an input unit 40, an air-conduction hearing tester 50, a bone-conduction hearing tester 60, a masking tester 70, and a controller 80.

The display unit 10 displays a use-procedure guide or a test result. In an exemplary embodiment of the present invention, the display unit 10 may be a monitor for a computer. Alternatively, the display unit 10 may be a unit for printing a guide at one side of the device, turning a plurality of electric bulbs located at one side of the guide on for illuminating the guide according to a procedure, and displaying a test result on a liquid crystal display disposed at another side of the device.

When a control signal is input, the sound generating circuit 20 generates a sound in response to the input control signal. The control signal includes an indication of the frequency and intensity of the sound to be generated and an indication of whether the sound is to be generated toward any one of left and right ears. The sound generating circuit 20 generates the sound having the required frequency and intensity, and outputs the sound as an electrical signal. In the present invention, the sound generating circuit 20 may be a commercially available sound card for a computer.

The output unit 30 includes a headphone and a bone-conduction vibrator. The headphone converts the electrical signal from the sound generating circuit 20 into sound. The bone-conduction vibrator is mounted to a mastoid at a rear side of the ear, and converts the electrical signal from the sound generating circuit 20 into vibration and delivers the vibration toward the skull. The headphone and the bone-conduction vibrator vibrating and generating sound in response to the electrical signal from the sound generating circuit 20 is well known to those skilled in the art and a detailed description thereof will be omitted.

The input unit 40 allows the user to indicate that he/she has heard the sound from the output unit 30. In the exemplary embodiment of the present invention, the input unit 40 is a keyboard for a computer. Alternatively, the input unit 40 may be a switch or a touch screen.

The air-conduction hearing tester 50 will now be described. The air-conduction hearing tester 50 performs a hearing test in order to obtain the hearing threshold via a test to see whether the user can hear the pure tone propagated to his/her eardrum via his/her external auditory meatus by generating a pure tone to the headphone of the user. Specifically, the air-conduction hearing tester 50 generates a control signal to adjust sound pressure of the pure tone that is generated depending on a user's response input from the input unit 40. For example, the air-conduction hearing tester 50 outputs the control signal to increase the sound pressure to 45 dB when the user does not hear a 40 dB sound and to decrease the sound pressure to 35 dB when the user hears the 40 dB sound.

The air-conduction hearing tester 50 performs a hearing test on the left and right ears. First, the air-conduction hearing tester 50 generates a pure tone at a predetermined frequency. The air-conduction hearing tester 50 initially provides a predetermined sound pressure (40 dB) and increases or decreases the sound pressure at intervals of 5 dB depending on response. A minimum sound pressure of a sound that the user can hear is a hearing threshold. The test is performed with several frequencies to obtain a hearing threshold corresponding to each frequency.

The bone-conduction hearing tester 60 will now be described. The bone-conduction hearing tester 60 performs a hearing test on the user by using the sound propagated through the skull. The air-conduction hearing test cannot exactly perform the hearing test when the user suffers from an external or middle ear disease, such as an external ear disease induced change or a middle ear inflammation. In this case, it is necessary to perform the hearing test based on vibration propagated via the skull. The bone-conduction hearing tester 60 sends an electrical signal to the bone-conduction vibrator rather than the headphone so that the bone-conduction vibrator generates a vibration-induced pure tone, and obtains an ear's bone-conduction hearing threshold. Since the bone-conduction hearing tester 60 performs the test in the same process as the air-conduction hearing tester 50, a detailed description of the test process of the bone-conduction hearing tester 60 will be omitted.

The masking tester 70 will now be described. The masking tester 70 performs the hearing test by generating a noise toward a headphone mounted to one ear and a pure tone to the other ear to be measured. When there is a great difference between the hearings of both ears, this hearing test is intended to prevent the sound from being delivered to the good ear via the skull instead of via an external auditory meatus. In general, the masking tester 70 is activated when there is a difference of 35 dB or more between both ears in the air-conduction hearing test or when there is a difference of 15 dB or more between the air-conduction hearing threshold of the bad ear and the bone-conduction hearing threshold of the good ear in the bone-conduction hearing test. When masking bone-conduction hearing, the masking tester 70 determines an ear on which the headphone will be mounted and an ear to which the bone-conduction vibrator will be attached, and outputs a control signal to display the determination result on the display unit 10. The masking tester 70 generates a control signal to increase sound pressure of the noise when the user hears the pure tone and to increase the pure tone when the user does not hear the pure tone.

The controller 80 will now be described. The controller 80 is connected to and controls the display unit 10, the sound generating circuit 20, the input unit 40, the air-conduction hearing tester 50, the bone-conduction hearing tester 60, and the masking tester 70. The controller 80 receives a control signal for the frequency and the sound pressure for testing from the air-conduction hearing tester 50, the bone-conduction hearing tester 60, and the masking tester 70, converts the control signal to be suitable for reception by the sound generating circuit 20, and sends the control signal to the sound generating circuit 20. Here, since the control signal depends on a type of commercially available sound card as the sound generating circuit 20 the controller 80 converts the control signal as mentioned above. The controller 80 controls the display unit 10 to display a guide for any procedure required to perform the hearing test. For example, in the masking test, the controller 80 controls the monitor to display on the screen an ear on which the headphone will be mounted and an ear to which the bone-conduction vibrator will be attached, such that the user correctly mounts the headphone and the bone-conduction vibrator. The controller 80 also receives a signal from the input unit 40 and sends the signal to the air-conduction hearing tester 50, the bone-conduction hearing tester 60, and the masking tester 70.

Here, the controller 80 further includes a storage unit 82 for storing the test result so that a type and degree of hearing loss is displayed and the test result can be checked by the user at anytime.

The controller 80 stores information on the sound generating circuit 20 and the headphone and the bone-conduction vibrator of the output unit 30. This is because the sound generating circuit 20, the headphone, and the bone-conduction vibrator have different features depending on make or model, and therefore, the controller 80 cannot generate an accurate sound by using the same control signal. Accordingly, it is necessary to recognize the features of the sound generating circuit 20, the headphone, and the bone-conduction vibrator by performing a test in advance. Specifically, the controller 80 measures an electrical signal, sound or vibration output while increasing or decreasing sound pressure for each frequency, determines a value to be corrected for each frequency with respect to each device, and stores the value in a database 84. The controller 80 reads a correction value for the type of corresponding device and performs correction by applying the correction value. For example, when the connected headphone generates a signal at 1000 Hz to output 35 dB, a non-corrected signal may be output at 30 dB. In this case, the controller 80 controls the sound generating circuit to generate a 35 dB signal, such that an output signal of the headphone is 35 dB.

Operation and effects of the pure tone audiometer according to an exemplary embodiment of the present invention will now be described in detail with reference to FIG. 1.

Using the keyboard, a user inputs the type of sound generating circuit 20 mounted on the pure tone audiometer of the present invention by viewing the screen of the display unit 10. The user also inputs make and model names of the headphone and the bone-conduction vibrator connected to the sound generating circuit 20 so that the controller 80 performs the correction.

When there is a request from the user for a pure tone hearing test, the controller 80 sends a control signal to control the air-conduction hearing tester 50 to perform a testing procedure. The air-conduction hearing tester 50 displays a guide to instruct the user to wear the headphone on the display unit 10 via the controller 80. When the user wears the headphone according to the guide and presses an enter key of the keyboard, an input signal from the keyboard is sent to the air-conduction hearing tester 50 via the controller 80, such that the hearing test is initiated.

The air-conduction hearing tester 50 instructs the user to select an ear with good hearing, and begins to first test the selected ear. The air-conduction hearing tester 50 generates a pure tone at 1000 Hz to output 40 dB, and outputs it to the selected ear. When the user hears the sound and presses a predetermined button, the air-conduction hearing tester 50 decreases the pure tone by an interval of 5 dB. When the user does not hear the sound (i.e., the user does not press the button for a predetermined time), the air-conduction hearing tester 50 increases the pure tone by an interval of 5 dB. The air-conduction hearing tester 50 performs this process repeatedly three times in order to obtain the threshold. When the two or more responses from the user are the same, the air-conduction hearing tester 50 determines the smallest value to be the threshold. The test is first performed at 1000 Hz. The test is then performed at 2000 Hz, 3000 Hz, 4000 Hz, and 8000 Hz. A threshold at 1000 Hz is obtained again. When a difference between the threshold at 1000 Hz and an initial threshold is 10 dB or more, the test is performed again at the higher frequencies. When the difference is less than 5 dB, the test is performed at lower frequencies in the order of 500 Hz, 250 Hz, and 125 Hz.

This process is then performed on the other ear to obtain the air-conduction hearing threshold of both ears. When a difference between both hearing thresholds is 35 dB or more, the controller 80 calls the masking tester 70. The masking tester 70 sends a noise to the good ear and a pure tone to the bad ear, and increases or decreases the sound pressure of the noise or pure tone depending on a response from the user in order to test the hearing.

The pure tone audiometer then performs the bone-conduction hearing test on a user who is likely to suffer from hearing loss or is suffering from middle ear inflammation. The bone-conduction hearing test includes sending vibration via the bone-conduction vibrator attached to the rear of the ear, not via the headphone, and detecting the vibration propagated via the skull. The bone-conduction hearing test includes measuring only frequencies from 250 Hz to 4000 Hz. Since this testing process is the same as the process of obtaining the air-conduction hearing threshold, a detailed description thereof will be omitted.

When a difference between the air-conduction hearing threshold of the bad ear and the bone-conduction hearing threshold of the good ear, which are sequentially measured, is 15 dB or more, the controller 80 calls the masking tester 70. The masking tester 70 instructs the user to attach the bone-conduction vibrator to the ear to be tested and wear the headphone on the other ear, and then sends a noise to the headphone and a pure tone to the bone-conduction vibrator for hearing testing.

The test result may be displayed on the screen of the display unit 10. The test result may be output by a printer, if necessary.

Such a test can provide accurate air-conduction and bone-conduction hearing thresholds, such that hearing loss can be prevented and early detection is possible without assistance from a doctor or an audiologist.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A pure-tone audiometer apparatus comprising:
a display unit configured to display at least one of a use-procedure guide and a test result of a pure-tone hearing test;
a sound-generating circuit configured to selectively output an electrical signal in response to a sound-generating control signal;
an output unit including a headphone and a bone-conduction vibrator, wherein the output unit is coupled to receive the electrical signal from the sound-generating circuit, and wherein the output unit is configured to generate, in response to the electrical signal, at least one of a pure tone and a masking sound for the pure-tone hearing test;
an input unit configured to receive, from a user, a user response based on the user's hearing the pure tone generated by the output unit and to generate an input signal based on the user response received from the user;
an air-conduction hearing tester (ACHT) configured to control a first part of the pure-tone hearing test, wherein the first part of the pure-tone hearing test is based on the pure tone generated by the output unit when the electric signal is coupled to the headphone and the pure tone is output from the headphone and propagated via an external auditory meatus, wherein the ACHT outputs an ACHT control signal that causes the headphone of the output unit to selectively output the pure tone into air as an air pure tone to the user's left ear and to the user's right ear, and wherein the ACHT adjusts the air pure tone depending on the user response received from the user to obtain a measured air-conduction hearing threshold for each ear, and wherein when the measured air-conduction hearing threshold for each ear determines the left ear has better hearing than the right ear, then the left ear is determined to be a good ear having better hearing and the right ear is determined to be a bad ear having worse hearing, and when the measured air-conduction hearing threshold for each ear determines the right ear has better hearing than the left ear, then the right ear is determined to be the good ear having better hearing and the left ear is determined to be the bad ear having worse hearing;
a bone-conduction hearing tester (BCHT) configured to control a second part of the pure-tone hearing test, wherein the second part of the pure-tone hearing test is based on the pure tone generated by the output unit when the electric signal is coupled to the bone-conduction vibrator and the pure tone is output from the bone-conduction vibrator and propagated through the user's skull, wherein the BCHT outputs a BCHT control signal that causes the bone-conduction vibrator of the output unit to selectively output the pure tone as a conducted vibration pure tone to the user's left ear and to the user's right ear, and wherein the BCHT adjusts the vibration pure tone depending on the user response received from the user to obtain a measured bone-conduction hearing threshold for each ear;
a masking tester (MT) configured to control a masked part of the pure-tone hearing test, wherein the MT outputs an MT control signal that causes the masking sound to be coupled to the one ear having better hearing (the good ear) and the pure tone to the other ear when there is at least a first value of dB difference in the air-conduction hearing threshold between the user's left ear hearing and the user's right ear hearing measured by the ACHT, and wherein the MT outputs the MT control signal that causes the masking sound to be coupled to the good ear and the pure tone to be coupled to the other ear when there is at least a second value of dB difference in hearing threshold between the air-conduction hearing threshold of the ear having worse hearing (the bad ear) measured by the ACHT and the bone-conduction hearing threshold of the good ear measured by the BCHT; and
a controller operatively coupled to the display unit, to the ACHT, to the BCHT, to the MT, and to the sound-generating circuit, wherein the controller is configured to control the sound-generating circuit to generate the pure tone and the masking sound in response to control signals from the ACHT, the BCHT, and the MT, and is configured to receive the input signal from the input unit and to send the input signal to the ACHT, the BCHT, and the MT, wherein the ACHT, the BCHT, and the MT are configured to determine the test result of the pure-tone hearing test based on the user response received from the user from the input unit, and wherein the controller is configured to output a display control signal to control the display unit to display the use-procedure guide and the test result.

2. The pure tone audiometer apparatus of claim 1, wherein the controller further includes a storage unit operatively coupled to store the test result of the pure tone hearing test, and wherein a type and degree of hearing loss are displayed at a later time.

3. The pure tone audiometer of apparatus claim 1, wherein the controller further includes a feature database operatively coupled to store features of various types of sound-generating circuits, headphones, and bone-conduction vibrators, and outputs a different electrical signal depending on the sound-generating circuits, headphones, and bone-conduction vibrators used during the pure-tone hearing test.

4. The pure tone audiometer apparatus of claim 1, wherein the first value of dB difference is at least 35 dB.

5. The pure tone audiometer apparatus of claim 1, wherein the second value of dB difference is at least 15 dB.

6. The pure tone audiometer apparatus of claim 1, wherein the first part of the pure-tone hearing test is performed before the second part of the pure-tone hearing test.

7. The pure tone audiometer apparatus of claim 1, wherein the display unit includes a monitor of a computer.

8. The pure tone audiometer apparatus of claim 1, wherein the display unit is a printer.

9. The pure tone audiometer apparatus of claim 1, wherein the sound-generating circuit includes a commercially available sound card for a computer.

10. The pure tone audiometer apparatus of claim 1, wherein the input unit includes a keyboard of a computer.

11. The pure tone audiometer apparatus of claim 1, wherein the input unit includes a touch screen.

12. An audiometer apparatus comprising:
a display unit configured to display a test result of a pure-tone hearing test;
an output unit that includes a headphone and a bone-conduction vibrator, wherein the output unit is configured to selectively output, for the pure-tone hearing test, at least one of a pure-tone sound into air, a bone-conduction pure-tone vibration, and a masking sound into air;
an input unit configured to receive, from a user, a user response based on the user hearing the pure tone generated by the output unit and to generate an input signal based on the user response received from the user; and
a control system, wherein the control system is operatively coupled to the display unit, to the input unit, and to the output unit, and wherein the control system is
configured to selectively control the output unit to output the pure tone as a sound into air as an air pure-tone sound to the user's left ear and the user's right ear, and adjust the air pure-tone sound depending on the user response received from the user in order to determine a measured air-conduction hearing threshold for each ear, wherein when the measured air-conduction hearing threshold for each ear determines the left ear has better hearing than the right ear, then the left ear is determined to be the ear having better hearing and the right ear is determined to be the ear having worse hearing, and when the measured air-conduction hearing threshold for each ear determines the right ear has better hearing than the left ear, then the right ear is determined to be the having better hearing and the left ear is determined to be the ear having worse hearing;

configured to selectively control the output unit to output the pure tone as a bone-conducted vibration separately to the user's left ear and the user's right ear, and adjust the bone-conducted vibration pure tone depending on the user response received from the user to determine a measured bone-conduction hearing threshold for each ear;

configured to selectively control the output unit to output the masking sound into air to whichever ear has better hearing and the pure tone into air to whichever ear has worse hearing when there is at least a first value of dB difference between the air-conduction hearing threshold of the ear having better hearing and the air-conduction hearing threshold of the ear having worse hearing, and configured to selectively control the output unit to output the masking sound into air to the ear having better hearing and the pure tone as bone-conduction vibration to the ear having worse hearing when there is at least a second value of dB difference between the air-conduction hearing threshold of the ear having worse hearing and the bone-conduction hearing threshold of the ear having better hearing;

configured to determine the test result of the pure-tone hearing test based on the user response received from the user from the input unit; and configured to selectively control the display unit to display the test result.

13. The apparatus of claim 12, wherein the control system further includes:

a storage unit operatively coupled to store the test result of the pure tone hearing test, and wherein a type and degree of hearing loss are displayed at a later time; and a feature database operatively coupled to store features of various types of sound-generating circuits, headphones, and bone-conduction vibrators, and to differently control the control system depending on a particular sound-generating circuit, headphones, and bone-conduction vibrators used during the pure-tone hearing test.

14. The apparatus of claim 12, wherein the first value of dB difference is at least 35 dB, and wherein the second value of difference is at least 15 dB.

15. An automated pure-tone audiometer apparatus comprising:

a display unit;

means for selectively generating an electrical signal in response to a sound-generating control signal;

means for receiving the electrical signal and generating at least one of a pure tone transmitted through air, a pure tone transmitted through bone-conduction, and an air-transmitted masking sound transmitted through air;

means for receiving, from a user, a user response based on the user hearing at least one of the air pure tone and the bone-conduction pure tone, and means for generating an input signal based on the user response received from the user;

means for selectively performing an air-conduction hearing test as a first part of a pure-tone hearing test, wherein the air-conduction hearing test is based on the pure tone transmitted through air propagated via an external auditory meatus to the user's left ear and the user's right ear, and adjusting the air-transmitted pure tone depending on the user response received from the user to determine a measured air-conduction hearing threshold for each ear, wherein when the measured air-conduction hearing threshold for each ear determines the left ear has better hearing than the right ear, then the left ear is determined to be the ear having better hearing and the right ear is determined to be a bad ear having worse hearing, and when the measured air-conduction hearing threshold for each ear determines the right ear has better hearing than the left ear, then the right ear is determined to be the ear having better hearing and the left ear is determined to be the ear having worse hearing;

means for selectively performing a bone-conduction hearing test as a second part of the pure-tone hearing test, wherein the bone-conduction hearing test is based on the bone-conduction pure tone propagated through the user's skull to the user's left ear and the user's right ear, and adjusting the bone-conduction pure tone depending on the user response received from the user to determine a measured bone-conduction hearing threshold for each ear;

means for selectively performing a masked test as part of the pure-tone hearing test, wherein the masked test includes means for generating the air-transmitted masking sound to whichever ear has better hearing and the air-transmitted pure tone to whichever ear has worse hearing when there is at least a first value of dB difference between the air-conduction hearing threshold of the ear having better hearing and the air-conduction hearing threshold of the ear having worse hearing, and means for generating the air masking sound to the ear having better hearing and the bone-conduction pure tone to the other ear when there is at least a second value of dB difference between the air-conduction hearing threshold of the ear having worse hearing and the bone-conduction hearing threshold of the ear having better hearing;

means for determining a test result of the pure-tone hearing test based on the user response received from the user from the input unit; and means for displaying the test result on the display unit.

16. The pure-tone audiometer apparatus of claim 15, further comprising means for storing the test result of the pure tone hearing test and means for displaying the type and degree of hearing loss at a later time.

17. The pure-tone audiometer apparatus of claim 15, further comprising means for storing a feature database of various types of sound-generating circuits, headphones, and bone-conduction vibrators, and outputs a different electrical signal depending on the sound-generating circuits, headphones, and bone-conduction vibrators used during the pure-tone hearing test.

18. The pure-tone audiometer apparatus of claim 15, wherein the first value of dB difference is at least 35 dB.

19. The pure-tone audiometer apparatus of claim 15, wherein the second value of dB difference is at least 15 dB.

20. The pure-tone audiometer apparatus of claim 15, wherein the first part of the pure-tone hearing test is performed after the second part of the pure-tone hearing test.

* * * * *